United States Patent [19]

Furrer et al.

[11] Patent Number: 5,556,854
[45] Date of Patent: Sep. 17, 1996

[54] PYRIDOPYRIMIDINEDIONES, PROCESSES FOR THEIR PREPARATION AND THEIR USE AS DRUGS

[75] Inventors: Harald Furrer, Hofheim; Dirk Seiffge, Mainz-Kostheim; Ismahan Okyayuz-Baklouti; John J. Grome, both of Wiesbaden, all of Germany

[73] Assignee: Hoechst Aktiengesellschaft, Frankfurt am Main, Germany

[21] Appl. No.: 230,811

[22] Filed: Apr. 21, 1994

[30] Foreign Application Priority Data

Apr. 23, 1993 [DE] Germany ............ 43 13 317.7

[51] Int. Cl.$^6$ .............. C07D 471/04; C07D 211/78; A61K 31/505
[52] U.S. Cl. .............. 514/234.2; 514/258; 544/117; 544/279; 546/249; 546/310
[58] Field of Search .............. 544/279, 117; 514/258, 234.2

[56] References Cited

U.S. PATENT DOCUMENTS 3,186,991  6/1965  Ohnacker .............. 544/279

Primary Examiner—Mark L. Berch
Attorney, Agent, or Firm—Finnegan, Henderson, Farabow, Garrett & Dunner, L.L.P.

[57] ABSTRACT

Pyridopyrimidinediones, processes for their preparation and their use as drugs

A compound of the formula I:

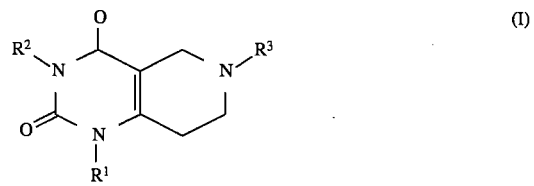

and/or physiologically acceptable salts of the compound of the formula I, and/or optionally stereoisomeric forms of the compound of the formula I, are suitable for the preparation of drugs for the treatment of circulatory disorders and/or neurodegenerative diseases.

6 Claims, No Drawings

PYRIDOPYRIMIDINEDIONES, PROCESSES FOR THEIR PREPARATION AND THEIR USE AS DRUGS

A number of 5,6,7,8-tetrahydropyrido[4,3-d]pyrimidines are known which can be active as antipyretics, antiphlogistics, diuretics, bacteriostats, sedatives and coronary artery dilators (U.S. Pat. No. 3,186,991).

It has now been found that the pyridopyrimidinediones according to the invention have a very good antithromboric action, promote the restoration of normal functions in ischemic muscles and have favorable effects on the energy metabolism in neuropathological syndromes. The pyridopyrimidinediones according to the invention are therefore suitable for use in the prophylaxis and/or therapy of circulatory disorders and/or neurodegenerative diseases.

The invention relates to the use of at least one compound of the formula I:

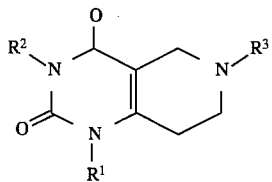

(I)

and/or a physiologically acceptable salt of the compound of the formula I, and/or an optionally stereoisomeric form of the compound of the formula I, in which $R^1$ is
a) a hydrogen atom,
b) $(C_1-C_4)$-alkyl,
c) ω-hydroxy-$(C_2-C_4)$-alkyl,
d) benzyl,
e) benzyl monosubstituted or polysubstituted on the ring by
  1) a halogen atom such as a fluorine, chlorine, bromine or iodine atom,
  2) nitrile or
  3) methoxy,
f) (ω-1)-$(C_3-C_5)$-alkenyl or
g) (ω-1)-$(C_3-C_5)$-alkenyl substituted on the carbon by methyl, $R^2$ is
a) a hydrogen atom,
b) $(C_1-C_6)$-alkyl,
c) benzyl or
d) benzyl monosubstituted or polysubstituted on the ring by
  1) a halogen atom such as a fluorine, chlorine, bromine or iodine atom,
  2) nitrile or
  3) methoxy and $R^3$ is
a) a hydrogen atom,
b) $(C_1-C_8)$-alkyl,
c) cyclohexylmethyl,
d) ω-hydroxy-$(C_2-C_8)$-alkyl,
e) (ω-1)-$(C_3-C_5)$-alkenyl,
f) (ω-1)-$(C_3-C_5)$-alkenyl substituted on the carbon by methyl,
g) benzyl,
h) benzyl 1) monosubstituted or polysubstituted on the ring by
  1.1 a halogen atom such as a fluorine, chlorine, bromine or iodine atom,
  1.2 nitrile,
  1.3 methoxy or
  1.4 —CH=CH—COOR⁴, in which $R^4$ is a hydrogen atom or $(C_1-C_4)$-alkyl,
and/or 2) monosubstituted in the α-position of the benzyl radical by
  2.1 methyl,
  2.2 hydroxymethyl,
  2.3 carboxyl or
  2.4

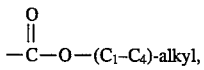

i) —$(CH_2)_n$—COOR⁵, in which n is an integer from i to 8 and $R^5$ is a) a hydrogen atom or b) $(C_1-C_4)$-alkyl,
k) —$CH_2$—CH=CH—COOR⁶, in which $R^6$ is $(C_1-C_4)$-alkyl,
l) pyridylmethyl,
m) 1-benzylimidazol-2-ylmethyl,
n) —CH(COOR⁶)₂, in which $R^6$ is $(C_1-C_4)$-alkyl
o) ω-morpholin-4-yl-$(C_2-C_4)$-alkyl,
p) 2-methylsulfinylethyl or
q) thienylmethyl (thenyl),
for the preparation of drugs for the prophylaxis and therapy of circulatory disorders and/or neurodegenerative diseases.

It is preferable to use at least one compound of the formula I, and/or a physiologically acceptable salt of the compound of the formula I, in which $R^1$ is
a) a hydrogen atom,
b) $(C_1-C_4)$-alkyl,
c) ω-hydroxy-$(C_2-C_4)$-alkyl,
d) benzyl,
e) benzyl monosubstituted or polysubstituted on the ring by
  1) a fluorine or chlorine atom,
  2) nitrile or
  3) methoxy,
f) (ω-1)-$(C_3-C_5)$-alkenyl or
g) (ω-1)-$(C_3-C_5)$-alkenyl substituted on the carbon by methyl, $R^2$ is
a) a hydrogen atom,
b) $(C_1-C_6)$-alkyl,
c) benzyl or
d) benzyl monosubstituted or polysubstituted on the ring by
  1) a fluorine or chlorine atom,
  2) nitrile or
  3) methoxy and $R^3$ is
a) a hydrogen atom,
b) $(C_1-C_8)$-alkyl,
c) cyclohexylmethyl,
d) ω-hydroxy-$(C_2-C_8)$-alkyl,
e) (ω-1)-$(C_3-C_5)$-alkenyl,
f) (ω-1)-$(C_3-C_5)$-alkenyl substituted on the carbon by methyl,
g) benzyl, h) benzyl 1) monosubstituted or polysubstituted on the ring by
1.1 a fluorine or chlorine atom,
1.2 nitrile,
1.3 methoxy or
1.4 —CH=CH—COOR$^4$, in which R$^4$ is a hydrogen atom or (C$_1$–C$_4$)-alkyl,
and/or 2) monosubstituted in the α-position of the benzyl radical by
2.1 methyl,
2.2 hydroxymethyl,
2.3 carboxyl,
2.4

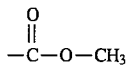

or
2.5

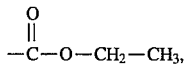

i) —(CH$_2$)$_n$—COOR$^5$, in which
n is an integer from I to 8 and
R$^5$ is a) a hydrogen atom or b) (C$_1$–C$_4$)-alkyl,
k) —CH$_2$—CH=CH—COOR$^6$, in which R$^6$ is (C$_1$–C$_4$)-alkyl,
l) 2-pyridylmethyl,
m) 1-benzylimidazol-2-ylmethyl,
n) —CH(COOR$^6$)$_2$, in which R$^6$ is (C$_1$–C$_4$)-alkyl,
o) ω-morpholin-4-yl-(C$_2$–C$_4$)-alkyl,
p) 2-methylsulfinylethyl or
q) 2-thienylmethyl (2-thenyl).

The term "benzyl" is understood as meaning a radical of the structure —CH$_2$—C$_6$H$_5$. The expression "benzyl substituted on the ring" denotes substitution of a hydrogen atom on the C$_6$H$_5$ moiety of the benzyl; the expression "monosubstituted in the d-position of the benzyl radical" denotes substitution of a hydrogen atom on the —CH$_2$ moiety of the benzyl.

The term "alkyl" is understood as meaning linear and branched hydrocarbon radicals.

The invention further relates to compounds of the formula I and physiologically acceptable salts of the compound of the formula I and optionally stereoisomeric forms of the compound of the formula I in which R$^1$ is
a) a hydrogen atom,
b) (C$_1$–C$_4$)-alkyl,
c) ω-hydroxy-(C$_2$–C$_4$)-alkyl,
d) benzyl,
e) benzyl monosubstituted or polysubstituted on the ring by
1) a halogen atom such as a fluorine, chlorine, bromine or iodine atom,
2) nitrile or
3) methoxy,
f) (ω-1)-(C$_3$–C$_5$)-alkenyl or
g) (ω-1)-(C$_3$–C$_5$)-alkenyl substituted on the (ω-1) carbon by methyl,
R$^2$ is
a) a hydrogen atom,
b) (C$_1$–C$_6$)-alkyl,
c) benzyl or
d) benzyl monosubstituted or polysubstituted on the ring by
1) a halogen atom such as a fluorine, chlorine, bromine or iodine atom,
2) nitrile or
3) methoxy and
R$^3$ is
a) a hydrogen atom,
b) (C$_1$–C$_8$)-alkyl,
c) cyclohexylmethyl,
d) ω-hydroxy-(C$_2$–C$_8$)-alkyl,
e) (ω-1)-(C$_3$–C$_5$)-alkenyl,
f) (ω-1)-(C$_3$–C$_5$)-alkenyl substituted on the carbon by methyl,
g) benzyl,
h) benzyl 1) monosubstituted or polysubstituted on the ring by
1.1 a halogen atom such as a fluorine, chlorine, bromine or iodine atom,
1.2 nitrile,
1.3 methoxy or
1.4 —CH=CH-COOR$^4$, in which R$^4$ is a hydrogen atom or (C$_1$–C$_4$)-alkyl, and/or 2) monosubstituted in the α-position of the benzyl radical by 2.1 methyl,
2.2 hydroxymethyl,
2.3 carboxyl or
2.4

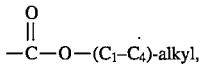

i) —(CH$_2$)$_n$—COOR$^5$, in which
n is an integer from i to 8 and
R$^5$ is a) a hydrogen atom or b) (C$_1$–C$_4$)-alkl,
k) —CH$_2$—CH=CH—COOR$^6$, in which R$^6$ is (C$_1$–C$_4$)-alkyl,
l) pyridylmethyl,
m) 1-benzlimidazol-2-ylmethyl,
n) —CH(COOR$^6$)$_2$, in which R$^6$ is (C$_1$–C$_4$)-alkl,
o) ω-morpholin-4-yl-C$_2$–C$_4$)-alkyl,
p) 2-methylsulfinylethyl or
q) thienylmethyl (thenyl),
with the exception of the compound of the formula I in which R$^1$ and R$^2$ are hydrogen atoms.

Preferred compounds of the formula I and physiologically acceptable salts of the compound of the formula I are those in which
R$^1$ is
a) a hydrogen atom,
b) (C$_1$–C$_4$)-alkyl,
c) ω-hydroxy-(C$_2$–C$_4$)-alkyl,
d) benzyl
e) benzyl monosubstituted or polysubstituted on the ring by a fluorine or chlorine atom,
f) (ω-1)-(C$_3$–C$_5$)-alkenyl or
g) (ω-1)-(C$_3$–C$_5$)-alkenyl substituted on the (ω-1) carbon by methyl,
R$^2$ is
a) a hydrogen atom,
b) (C$_1$–C$_6$)-alkyl,
c) benzyl or d) benzyl monosubstituted or polysubstituted on the ring by a fluorine or chlorine atom, and $R^3$ is a) a hydrogen atom,
b) $(C_1-C_8)$-alkyl,
c) cyclohexylmethyl,
d) ω-hydroxy-$(C_2-C_8)$-alkyl,
e) (ω-1)-$(C_3-C_5)$-alkenyl,
f) (ω-1)-$(C_3-C_5)$-alkenyl substituted on the (ω-1) carbon by methyl,
g) benzyl,
h) benzyl 1) monosubstituted or polysubstituted on the ring by
  1.1 a fluorine or chlorine atom,
  1.2 nitrile,
  1.3 methoxy or
  1.4 —CH=CH—COOR$^4$, in which R$^4$ is a hydrogen atom or $(C_1-C_4)$-alkyl,
and/or 2) monosubstituted in the α-position of the benzyl radical by
  2.1 methyl,
  2.2 hydroxyethyl,
  2.3 carboxyl,
  2.4

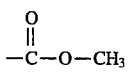

or
  2.5

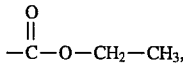, i) —(CH$_2$)$_n$—COOR$^5$, in which
  n is an integer from 1 to 8 and b) $(C_1-C_4)$-alkyl,
k) —CH$_2$—CH=CH—COOR$^6$, in which R$^6$ is $(C_1-C_4)$-alkyl,
m) 1-benzylimidazol-2-ylmethyl,
n) —CH(COOR$^6$)$_2$, in which R$^6$ is $(C_1-C_4)$-alkyl
o) ω-morpholin-4-yl-$(C_2-C_4)$-alkyl,
p) 2-methylsulfinylethyl or
q) 2-thienylmethyl (2-thenyl),
with the exception of the compound of the formula I in which $R^1$ and $R^2$ are hydrogen atoms.

Particularly preferred compounds of the formula I and physiologically acceptable salts of the formula I are those in which $R^1$ is
a) a hydrogen atom,
b) $(C_1-C_4)$-alkyl,
c) 2-hydroxyethyl,
d) benzyl or
e) 2-methylallyl, $R^2$ is
a) a hydrogen atom,
b) $(C_1-C_6)$-alkyl or
c) benzyl and $R^3$ is
a) a hydrogen atom,
b) $(C_1-C_8)$-alkyl,
c) cyclohexylmethyl,
d) ω-hydroxy-$(C_2-C_8)$-alkyl,
e) (ω-1)-$(C_3-C_5)$-alkenyl,
f) (ω-1)-$(C_3-C_5)$-alkenyl substituted on the (ω-1) carbon by methyl,
g) benzyl,
h) benzyl 1) monosubstituted or polysubstituted on the ring by
  1.1 a halogen atom such as a fluorine or chlorine atom,
  1.2 nitrile,
  1.3 methoxy or 1.4 —CH=CH—COOR$^4$, in which R$^4$ is methyl or ethyl, and/or 2) monosubstituted in the α-position of the benzyl radical by
  2.1 methyl,
  2.2 hydroxymethyl,
  2.3 carboxyl,
  2.4

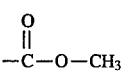

or
  2.5

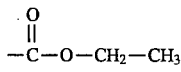

i) —(CH$_2$)$_n$—COOR$^5$, in which
  n is an integer from 1 to 8 and
  R$^5$ is a) a hydrogen atom or b) $(C_1-C_2)$-alkyl,
k) —CH$_2$—CH=CH—COOR$^6$, in which R$^6$ is $(C_1-C_2)$-alkyl,
l) 2-pyridylmethyl,
m) 1-benzylimidazol-2-ylmethyl,
n) —CH(COOR$^6$)$_2$, in which R$^6$ is $(C_1-C_2)$-alkyl,
o) ω-morpholin-4-ylethyl,
p) 2-methylsulfinylethyl or
q) 2-thienylmethyl (2-thenyl),
with the exception of the compound of the formula I in which $R^1$ and $R^2$ are hydrogen atoms.

Other preferred compounds of the formula I and physiologically acceptable salts of the compound of the formula I are those in which $R^1$ is
a) a hydrogen atom,
b) methyl or
c) ethyl, $R^2$ is
a) a hydrogen atom,
b) $(C_1-C_4)$-alkyl or
c) benzyl and $R^3$ is
a) a hydrogen atom,
b) $(C_1-C_8)$-alkyl,
c) cyclohexylmethyl,
d) ω-hydroxy-$(C_2-C_4)$-alkyl,
e) (ω-1)-$(C_3-C_5)$-alkenyl,
f) (ω-1)-$(C_3-C_5)$-alkenyl substituted on the carbon by methyl,
g) benzyl,
h) benzyl 1) monosubstituted or polysubstituted on the ring by
  1.1 a fluorine or chlorine atom, 1.2 nitrile,
1.3 methoxy or
1.4 —CH=CH—COOR⁴, in which R⁴ is methyl or ethyl, and/or 2) monosubstituted in the d-position of the benzyl radical by
2.1 carboxyl,
2.2

$$-\overset{O}{\underset{\|}{C}}-O-CH_3$$

or
2.3

$$-\overset{O}{\underset{\|}{C}}-O-CH_2-CH_3,$$

i) 2-thienylmethyl (2-thenyl),
with the exception of the compound of the formula I in which R¹ and R² are hydrogen atoms.

The invention further relates to processes for the preparation of the compound of the formula I, one embodiment comprising A) the reaction of a compound of the formula II:

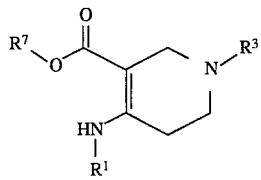

in which
R¹ is
  a) a hydrogen atom or
  b) (C₁–C₄)-alkyl,
R³ is
  a) (C₁–C₈)-alkyl,
  b) cyclohexylmethyl,
  c) benzyl monosubstituted or polysubstituted on the ring by a halogen atom or methoxy as in the formula I, or
  d) benzyl and
R⁷ is a lower alkyl radical, preferably methyl or ethyl, with a compound of the formula III:

$$R^2-N=C=y \qquad \text{(III)}$$

in which
R² is
  a) (C₁–C₆)-alkyl,
  b) benzyl monosubstituted or polysubstituted on the ring by a halogen atom or methoxy as in the formula I, or
  c) benzyl and
Y is an oxygen atom, to give a compound of the formula I:

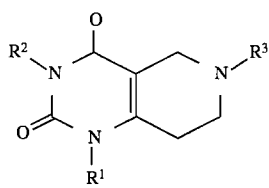

in which R² is as defined in the formula III and R¹ and R³ are as defined in the formula II, or B) the reaction of a compound of the formula II, in which R¹, R³ and R⁷ are as defined in the formula II, with a compound of the formula III, in which
R² is
  a) (C₁–C₆)-alkyl,
  b) benzyl monosubstituted or polysubstituted on the ring by a halogen atom or methoxy as in the formula I, or
  c) benzyl and
Y is a sulfur atom, to give a compound of the formula IV:

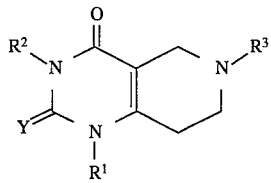

in which Y is a sulfur atom, R² is as defined in the formula III and R¹ and R³ are as defined in the formula II, and the oxidation of the compound of the formula IV to give a compound of the formula I, in which R² is as defined in the formula III and R¹ and R³ are as defined in the formula II, or c) the reaction of a compound of the formula I, in which R¹ is a hydrogen atom, (C₁–C₄)-alkyl or ω-hydroxy-(C₂–C₄)-alkyl, R² is a hydrogen atom, (C₁–C₆)-alkyl, benzyl or benzyl monosubstituted or polysubstituted on the ring by methoxy and R³ is a benzyl radical, to give a compound of the formula I, in which R³ is a hydrogen atom and R¹ and R² are as defined here for the compound of the formula I, or D) the reaction of a compound of the formula I and/or salts of the compound of the formula I, in which R¹ and/or R³ are hydrogen atoms and R² is as defined in the formula I, except for hydrogen, with a compound of the formula VII:

$$R^8-X \qquad \text{(VII)}$$

in which
X is
  a) a halogen atom such as a chlorine, iodine or bromine atom,
  b) a sulfonic acid ester radical or
  c) a phosphoric acid ester radical and
R⁸ is as defined for R¹ and R³ in the formula I, except for the hydrogen atom, those radicals R⁸ which carry an alcoholic hydroxyl group or a carboxyl group optionally being in protected form, and, after cleavage of the protecting group, conversion to a compound of the formula I, or E) the reaction of a compound of the formula I, in which R¹ and R² are as defined in the formula I, except for (ω-1)-(C₃–C₅)-alkenyl with hydrogen or methyl on the (ω-1) carbon atom, or benzyl monosubstituted or polysubstituted on the ring by nitrile or a bromine or iodine atom, and R³ is 2-methylsulfanylethyl, with an oxidizing agent, preferably a peracid, to give a compound of the formula I, in which R¹ and R² are as defined here for the compound of the formula I and R³ is 2-methylsulfinylethyl, or F) the reaction of a compound of the formula I, in which R¹ and R² are hydrogen atoms, alkyl or benzyl according to the formula I, and R³ is a hydrogen atom, with a compound of the formula V:

in which $R^9$ is a) a hydrogen atom, b) $(C_1-C_7)$-alkyl, c) cyclohexyl or d) phenyl, under reductive reaction conditions to give a compound of the formula I.

The procedure for process variant A is for example to prepare the compounds of the formula II by reacting substances of the formula VI with the amines $R^1$—$NH_2$ in suitable solvents, for example lower alcohols or a mixture thereof with water, at elevated temperatures, preferably between 40° C. and the boiling point of the solvent in question, $R^1$, $R^3$ and $R^7$ being as defined for the formula II.

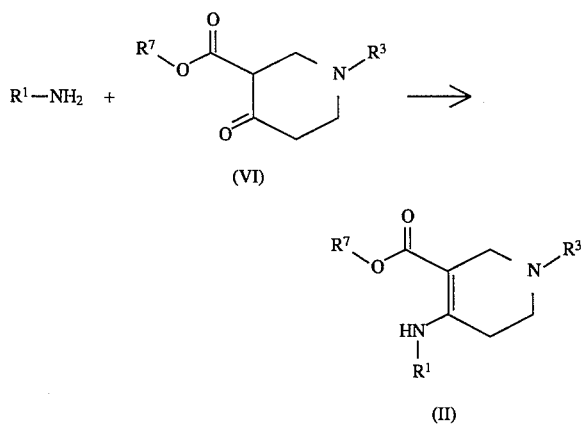

The substances of the formula VI are obtainable by known processes.

The reaction of the compounds of the formula II with the compounds of the formula III in which Y is an oxygen atom, to give compounds of the formula I, is carried out for example in an inert solvent, preferably toluene, in the presence of a tertiary amine, generally triethylamine, at elevated temperatures up to the boiling point of the solvent in question, optionally under elevated pressure, this being followed by an aftertreatment under alkaline conditions, preferably using sodium ethylate in a suitable solvent, advantageously ethanol, at elevated temperature, preferably under reflux conditions.

The procedure for process variant B is as for process variant A, Y being a sulfur atom in the compound of the formula III. An aftertreatment under alkaline conditions is not necessary. The oxidation of the compound of the formula IV in which Y=a sulfur atom is carried out for example in an alkaline medium with hydrogen peroxide.

In process variant C, the debenzylation is carried out under conventional conditions, preferably by catalytic hydrogenolysis in the presence of noble metal catalysts, generally palladium or platinum, in solvents such as methanol, ethanol or glacial acetic acid, at normal pressure or elevated pressure, preferably at pressures from 1 to 5 bar, and at temperatures from room temperature to 80° C.

In process variant D, the reaction is carried out in inert dispersing agents or solvents. Particularly suitable dispersing agents or solvents are dipolar aprotic solvents, for example dimethylformamide, dimethylacetamide, acetone or methyl ethyl ketone, but it is also possible to use alcohols such as methanol or ethanol, or halogenated hydrocarbons such as dichloromethane or chloroform. These reactions are conveniently carried out in the presence of a basic agent. Suitable basic agents are especially alkali metal or alkaline earth metal hydroxides, carbonates, alcoholares or hydrides in the case where $R^1$=H is replaced with one of the radicals mentioned for $R^1$ in the formula I, and organic bases, preferably ethyldiisopropylamine, diazabicyclononene or diazabicycloundecene, in the case where hydrogen is replaced in the position of $R^3$.

However, the compounds of the formula I in which $R^1$=H can also be used directly in the alkylation reaction in the form of their specially prepared salts, for instance the alkali metal or alkaline earth metal salts. The introduction of the alkyl radicals according to the procedures described above is generally carried out at a reaction temperature between room temperature and the boiling point of the solvent in question, preferably between 20° C. and 100° C.

The protection of those alkylating agents Rs-X which contain an alcoholic hydroxyl group or a carboxyl radical, and the possible cleavage of the protecting group in question following alkylation to form compounds of the formula I, are carried out by known methods.

The alcoholic hydroxyl radical in the compounds $R^8$—X is preferably protected with 2,3-dihydropyran or isopropenyl methyl ether by reaction in an acid medium, generally at room temperature in an inert solvent, for example dichloromethane, and, after alkylation, the protecting group is preferably removed by hydrolysis or methanolysis in an acid medium to give the compounds of the formula I with an alcoholic functional group on the substituent in the position of $R^1$ and/or $R^3$.

The carboxylic acid radical in the compounds $R^8$—X is preferably protected in the form of $(C_1-C_4)$-alkyl carboxylates, which are prepared in a known manner. The tert-butyl carboxylates are advantageously obtained by reacting the corresponding carboxylic acids with isobutylene in an acid medium, preferably in dichloromethane in the presence of sulfuric acid. The conversion of the carboxylic acid esters of the formula I to the corresponding carboxylic acids is carried out by conventional methods, the reaction in the case of the tert-butyl carboxylates preferably being carried out in dichloromethane with hydrogen chloride at temperatures of 0°–5° C.

In process variant E, the oxidation is carried out for example by means of hydrogen peroxide in acetone or glacial acetic acid or by means of tetrabutylammonium periodate in chloroform, but preferably by means of organic peracids, such as magnesium monoperoxyphthalate, in ethanol. The reaction temperatures are between 0° C. and the boiling point of the solvent in question, but preferably 0° C. to 60° C.

In process variant F, the reaction is carried out by the known method of reductive alkylation with an aldehyde $R^9$—CHO. The principal reducing agents used are catalytically activated hydrogen and formic acid and derivatives thereof (Leuckart-Wallach reaction).

The invention further relates to drugs containing an effective amount of at least one compound of the formula I or one of its physiologically acceptable salts, in addition to pharmaceutically appropriate and physiologically acceptable excipients, additives and/or other active ingredients and adjuncts.

The drugs according to the invention can be administered orally, topically, rectally, intravenously or else, if appropriate, parenterally.

The drugs according to the invention are preferably suitable for the prophylaxis and/or therapy of circulatory and metabolic disorders, especially microcirculatory disorders and diseases resulting therefrom.

The diseases resulting from circulatory disorders, especially from microcirculatory disorders, are mainly ischemic skeletal and/or myocardial diseases, especially claudicatio intermittens, ulcus cruris and degenerative and/or inflammatory myopathy of diverse origin with or without muscular atrophy, vasculitis with thrombotic incidents, and arterial and venous thrombi, e.g. thrombosis, shock or infaration.

Because of the circulation-stimulating action of the compounds and drugs according to the invention, especially on the microcirculation, the compounds and drugs are also effective in arteriosclerosis, in postoperative treatment for preventing postoperative thrombosis, in the aftertreatment of cancer for preventing or reducing the formation of metastases, in the treatment of patients dependent on heart-lung machines or renal dialysis, and finally also in the treatment of patients after transient ischemic attacks (TIA), stroke or cardiac infarction, as well as for wound healing following trauma and exogenous noxae.

The drugs according to the invention are also suitable for the prophylaxis and/or therapy of neurodegenerative diseases in humans and animals. A large number of neuropathological situations are characterized by a degeneration and the loss of neurones. This applies especially to neurodegenerative syndromes such as stroke, temporary cerebral ischemia (TIA), cerebral infarction with only partially reversible symptoms (PRIND), cerebral palsy, cerebral hypoglycemia, ischemic incidents during cardiac arrest or surgical interventions in the heartlung region, anoxic states, for example after drowning, intoxication or spinal cord injuries, perinatal asphyxia, neurodegenerative changes caused by old age, Alzheimer's disease (SDAT), pain, hypersecretion of growth hormone and luteinizing hormone, schizophrenia, epilepsy, Huntington's chorea and other chronic neurodegenerative diseases.

The invention further relates to a process for the preparation of a drug according to the invention, which comprises converting at least one compound of the formula I to a suitable form of administration with a pharmaceutically appropriate and physiologically acceptable excipient and optionally other appropriate active ingredients, additives or adjuncts.

Examples of suitable solid or liquid galenic formulations are granules, powders, coated tablets, tablets, (micro) capsules, suppositories, syrups, juices, suspensions, emulsions, drops or injectable solutions, as well as preparations with prolonged release of the active ingredient, which are produced using conventional auxiliaries such as excipients, disintegrants, binders, coatings, swelling agents, lubricants, flavorings, sweeteners and solubilizers. Frequently used adjuncts which may be mentioned are e.g. magnesium carbonate, titanium dioxide, lactose, mannitol and other sugars, talc, lactalbumin, gelatin, starch, cellulose and derivatives thereof, animal and vegetable oils such as cod-liver oil, sunflower oil, groundnut oil or sesame oil, polyethylene glycols and solvents such as sterile water and monohydric or polyhydric alcohols, e.g. glycerol.

The pharmaceutical preparations are preferably produced and administered in dosage units, each unit containing a specific dose of the compound of the formula I according to the invention as the active constituent. This dose can be up to about 1000 mg, but preferably about 50 to 300 mg, in the case of solid dosage units such as tablets, capsules, coated tablets or suppositories, and up to about 300 mg, but preferably about 10 to 100 mg, in the case of injectable solutions in ampoule form.

For the treatment of an adult patient weighing about 70 kg, the indicated daily doses for humans and animals depending on the activity of the compounds of the formula I - are from about 50 to 3000 mg of active ingredient, preferably about 150 to 1000 mg, in the case of oral administration, and from about 50 to 1000 mg, preferably about 100 to 300 mg, in the case of intravenous administration. Under certain circumstances, however, higher or lower daily doses can also be used. The daily dose can be administered either as a single administration in the form of an individual dosage unit or several smaller dosage units, or else as a multiple administration of divided doses at specific intervals. Finally, in the preparation of the abovementioned galenic forms of administration, the compounds of the formula I and/or their physiologically acceptable salts, if appropriate, can also be formulated together with other suitable active ingredients, for example circulationstimulating substances, platelet aggregation inhibitors, thrombocyte aggregation inhibitors and calcium antagonists, antithrombotics, antihyperlipidemics, neuroprotectors, analgesics, sedatives, antidepressants, antiinflammatories, antianginal agents, cardiotonics, antiarrhythmics, diuretics, antihypertensives including β-receptor and calcium blockers, plasma expanders and other vasotherapeutic agents.

EXAMPLES

The structure of all the compounds described below was confirmed by means of $^1$H NMR and IR spectra, in some cases also by means of mass spectra, and by means of elemental analyses.

Abbreviations:

a analogously to coIIc. concentrated

DMF dimethylformamide

GC gas chromatography ip intraperitoneal iv intravenous m.p. melting point or start of decomposition (d)

po per os

PVD peripheral vascular disease sc subcutaneous

Example 1

3-Methyl-5,6,7,8-tetrahydro-1H-pyrido[4,3-d]pyrimidine- 2,4-dione hydrochloride a) Methyl 4-amino-1-benzyl-1,2,5,6-tetrahydropyridine-3-carboxylate 855 g of methyl 1-benzyl-4-oxopiperidine-3-carboxylate hydrochloride, 176 g of sodium carbonate and 450 ml of 25% aqueous ammonia solution in 6.5 l of ethanol were heated for 5 h at an internal temperature of 70° C., with stirring. After concentration under reduced pressure, the mixture was worked up by extraction with dichloromethane and water. The combined dichloromethane phases were dried over sodium sulfate and concentrated under reduced pressure to give 788 g of oily methyl 4-amino- 1-benzyl-1, 2,5,6-tetrahydropyridine-3-carboxylate as a crude product, which was used in Example 1b) without further purification.

b) 6-Benzyl-3-methyl-2-thioxo-2,3,5,6,7,8-hexahydro-1H-pyrido[4,3-d]pyrimidin-4-one 788 g of methyl 4-amino-1-benzyl-1,2,5,6-tetrahydropyridine- 3-carboxylate from a) were dissolved in 2.5 l of toluene, and 447 g of methyl isothiocyanate and 625 ml of triethylamine were added, with stirring. After stirring for 24 h at an internal temperature of 100° C., the mixture was allowed to cool to 20° C. and the precipitate was filtered off with suction and washed with toluene. After drying, this gave 420 g of crude 6 benzyl-3-methyl- 2-thioxo-2,3,5,6,7, 8-hexahydro-1H-pyrido[4,3-d]pyrimidin- 4-one, which was reacted further in c).

Decomposition point: 210° C. $C_{15}H_{17}N_3OS$ (MW=287.39) Calc. C 62.69% H 5.96% N 14.62% S 11.16% Found C 62.66% H 6.03% N 14.62% S 11.26% c) 6-Benzyl-3-methyl-5,6,7,8-tetrahydro-1H-pyrido[4,3-d]pyrimidine-2,4-dione 3.2 l of 30% hydrogen peroxide were added dropwise at 0° C. over a period of 5½ h, with stirring, to a suspension of 210 g of 6-benzyl-3-methyl-2-thioxo- 2,3,5,6,7,8-hexahydro-1H-pyrido[4,3-d]pyrimidin-4-one from b) in a solution of 78 g of NaOH in 4 l of water. After subsequent stirring for ½ hour at 0° C., the pH of 9.7 was adjusted to 7.4 with conc. hydrochloric acid and the precipitate was filtered off, washed with water and dried. The above preparation was repeated and the precipitates were combined (396 g). These were purified by suspension in I l of water and dissolution with 33% sodium hydroxide solution (pH 13.5). Activated charcoal was added, with stirring, the mixture was filtered and the filtrate was adjusted to pH 10. The precipitate formed was filtered off with suction, washed with water and dried under reduced pressure to give 192 g of 6-benzyl-3-methyl-5,6,7,8-tetrahydro-1H-pyrido[4,3-d]pyrimidine-2,4-dione, which was debenzylated by hydrogenolysis in d).

d) 3-Methyl-5, 6,7,8-tetrahydro-1H-pyrido[4,3-d]pyrimidine-2,4-dione

A solution of 96 g of 6-benzyl-3-methyl-5,6,7,8-tetrahydro- 1H-pyrido[4,3-d]pyrimidine-2,4-dione from c) in 1.5 l of glacial acetic acid was debenzylated by hydrogenolysis for 6 h on 14.6 g of 10% palladium/activated charcoal at 25° C. and 3.5 bar. After the catalyst had been filtered off, the filtrate was concentrated under reduced pressure. The above preparation was repeated. The two crude products were combined, dissolved in water and precipitated, with stirring, by the addition of 33% sodium hydroxide solution to pH 6.9. The precipitate was washed with water and dried at 60° C. under reduced pressure to give 115.3 g of 3-methyl-5,6,7, 8-tetrahydro-1H-pyrido[4,3-d]pyrimidine-2,4-dione.

e) 3-Methyl -5,6,7,8-tetrahydro-1H-pyrido[4,3-d]-pyrimidine-2,4-dione hydrochloride 7.5 g of 3-methyl-5,6,7,8-tetrahydro-1H-pyrido[4,3-d]-pyrimidine- 2,4-dione were dissolved in ethanol and precipitated as the hydrochloride with a 50% excess of a solution of HCl in ether. The precipitate was recrystallized from methanol/diethyl ether.

Yield: 7 g Decomposition point: 304° C. $C_8H_{12}ClN_3O_2$ (MW=217.7) Calc. C 44.15% H 5.56% Cl 16.29% N 19.31% Found C 44.21% H 5.68% Cl 16.11% N 19.21%

Example 2

6-Benzyl-3-methyl-5,6,7,8-tetrahydro-1H-pyrido[4,3-d]-pyrimidine-2,4-dione hydrochloride a) 6-Benzyl-3-methyl-5,6,7,8-tetrahydro-1H-pyrido[4,3d]-pyrimidine- 2,4-dione In a 5 l steel autoclave, 530 g of methyl 4-amino-1-benzyl-1,2,5,6-tetrahydropyridine-3-carboxylate are shaken for 8 h at 100° C. with 510 ml of methyl isocyanate and 48 g of triethylamine in 2 l of dry toluene under nitrogen. After cooling, the reaction mixture was concentrated under reduced pressure. The residue was dissolved in 500 ml of ethanol, 154 g of sodium ethylate in 1.5 l of ethanol were added and the mixture was heated for 2 h at the reflux temperature, with stirring. After concentration of this mixture under reduced pressure, the residue was worked up by extraction with dichloromethane and water and the combined aqueous phases (pH=12.5) were adjusted to pH 10 with conc. hydrochloric acid, with stirring. The precipitate of 6-benzyl-3-methyl- 5,6,7,8-tetrahydro-1H-pyrido[4,3-d] pyrimidine-2,4-dione was filtered off, washed with water until the washings were neutral, and dried at 50° C. under reduced pressure.

Yield: 179.6 g b) 6-Benzyl-3-methyl-5,6,7,8-tetrahydro-1H-pyrido[4,3-d]pyrimidine-2,4-dione hydrochloride 14.3 g of 6-benzyl-3-methyl-5,6,7,8-tetrahydro- 1H-pyrido[4,3-d]pyrimidine-2,4-dione were dissolved in 300 ml of dichloromethane, and 6-benzyl-3-methyl- 5,6,7,8-tetrahydro-1H-pyrido[4,3-d]pyrimidine-2,4-dione hydrochloride was precipitated with a solution of hydrochloric acid in ether, while cooling with ice. The product was purified by recrystallization from isopropanol.

Yield: 12.4 g Decomposition point: 298° C. $C_{15}H_{18}ClN_3O_2$ (MW=307.78) Calc. C 58.54% H 5.90% Cl 11.52% N 13.65% Found C 58.34% H 5.84% Cl 11.33% N 13.61%

Example 3

6-Benzyl-1,3-dimethyl-5,6,7,8-tetrahydro-1H-pyrido[4,3-d]pyrimidine-2,4-dione hydrochloride 9.6 ml of methyl iodide were added dropwise at 40° C. over a period of 10 minutes, with stirring, to 40.7 g of 6-benzyl-3-methyl-5,6,7,8-tetrahydro-1H-pyrido[4,3-d]pyrimidine-2,4-dione and 20.7 g of potassium carbonate in 230 ml of dimethylformamide. After heating for 8 hours at 60° C., the mixture was concentrated under reduced pressure, the residue was taken up with water, the pH was adjusted to 8 and the mixture was worked up by extraction with dichloromethane and water. After the combined dichloromethane phases had been concentrated under reduced pressure, the residue was purified by chromatography on silica gel with dichloromethane/ethanol (volume ratio 95:5) to give 16.5 g of 6-benzyl- 1,3-dimethyl-5,6,7,8-tetrahydro-1H-pyrido[4, 3-d]pyrimi-dine-2,4-dione, from which 6-benzyl- 1,3-dimethyl-5,6,7,8-tetrahydro-1H-pyrido[4,3-d]pyrimidine-2,4-dione hydrochloride was obtained as a precipitate in diethyl ether with a solution of hydrochloric acid in ether. The product was recrystallized from methanol/diethyl ether and residual methanol was removed by the addition of water to the precipitate, concentration under reduced pressure and drying of the residue under high vacuum.

Yield: 15.1 g M.p.: 141°–143° C. $C_{16}H_{20}ClN_3O_2$ with 1.2 $H_2O$ (MW=343.43) Calc. C 55.96% H 6.57% Cl 10.32% N 12.24% Found C 56.09% H 6.39% Cl 10.15% N 12.17%

Example 4

3,6-Dibenzyl-5,6,7,8-tetrahydro-1H-pyrido[4,3-d]pyrimidine- 2,4-dione hydrochloride A mixture of 165 g of methyl 4-amino-1-benzyl- 1,2,5, 6-tetrahydropyridine-3-carboxylate, 68 g of triethylamine and 100 g of benzyl isocyanate in 700 ml of toluene was heated at the reflux temperature for 8 h, with stirring. After cooling, the reaction mixture was concentrated under reduced pressure. The residue was dissolved in 300 ml of ethanol, 58 g of sodium ethylate in 400 ml of ethanol were added and the mixture was heated at 80° C. for 1.5 h, with stirring. After this mixture had been concentrated under reduced pressure, the residue was worked up by extraction with dichloromethane and water and the combined and dried dichloromethane extracts were concentrated under reduced pressure. The combined aqueous phases were adjusted to pH 7 with conc. hydrochloric acid. After drying, the precipitate formed was combined with the concentrated dichloromethane extracts and the mixture was purified by recrystallization from ethanol to give 81 g of 3,6-dibenzyl-5,6,7, 8-tetrahydro-1H-pyrido[4,3-d]pyrimidine- 2,4-dione. 10 g of this base were dissolved in dichloromethane and the hydrochloride was precipitated by the addition of a solution of hydrochloric acid in ether. Recrystallization from ethanol/water (volume ratio 1:1) gave 10.1 g of 3,6-dibenzyl-5,6,7, 8-tetrahydro- 1H-pyrido[4,3-d]pyrimidine-2,4-dione hydrochloride.

Decomposition point: 300° C. $C_{21}H_{22}ClN_3O_2$ (MW= 383.88) Calc. C 65.71% H 5.78% Cl 9.24% N 10.95% Found C 65.54% H 5.82% Cl 9.06% N 10.87%

Example 5

Ethyl (3-methyl-2,4-dioxo-2,3,4,5,7,8-hexahydro-1H-pyrido[4,3-d]pyrimidin-6-yl)phenylacetate hydrochloride 11 g of 3-methyl-5,6,7,8-tetrahydro-1H-pyrido[4,3-d]-pyrimidine-2,4-dione, 12.7 g of ethyl chlorophenylacetate and 8.3 g of ethyldiisopropylamine in 250 ml of dimethylformamide were stirred for 48 h at room temperature. After concentration under vacuum, the mixture was worked up by extraction with dichloromethane and water. After drying and removal of the solvent, the dichloromethane phases yielded 26.6 g of an oily residue, from which 20.9 g of ethyl (3-methyl-2,4-dioxo- 2,3,4,5,7,8-hexahydro-1H-pyrido[4,3-d]pyrimidin-6yl)phenylacetate hydrochloride were obtained after dissolution in 50 ml of dichloromethane and precipitation with a solution of hydrochloric acid in ether. The product was recrystallized from acetone/water.

Decomposition point: 166° C. $C_{18}H_{22}ClN_3O_4$ with 0.5 $H_2O$ (MW=388.86) Calc. C 55.60% H 5.96% Cl 9.12% N 10.81% Found C 55.77% H 5.92% Cl 9.02% N 10.81%

Example 6

(3-Methyl-2,4-dioxo-2,3,4,5,7,8-hexahydro-1H-pyrido[4, 3-d]pyrimidin-6-yl)phenylacetic acid hydrochloride 3.6 g of sodium hydroxide were added to a solution of 15.5 g of ethyl (3-methyl-2,4-dioxo- 2,3,4,5,7,8-hexa-hydro-1H-pyrido[4,3-d]pyrimidin-6-yl)phenylacetatein 150 ml of ethanol/water (volume ratio 1:1) and the mixture was heated for 3 h at the reflux temperature. After cooling, it was neutralized with 1 N hydrochloric acid and concentrated to dryness under reduced pressure. The residue was extracted several times by boiling with ethanol and the combined extracts were concentrated under reduced pressure to give 11.8 g, which were dissolved in 200 ml of methanol. (3-Methyl-2,4-dioxo- 2,3,4,5,7,8-hexahydro-1H-pyrido[4,3-d]pyrimidin-6-yl)phenylacetic acid hydrochloride was obtained as a white precipitate by the addition of ethanolic hydrochloric acid and was recrystallized from acetone/water.

Yield: 8.3 g Decomposition point: 237° C. $C_{16}H_{18}ClN_3O_4$ with 1.5 $H_2O$ (MW=378.82) Calc. C 50.73% H 5.59% Cl 9.36% N 11.09% Found C 50.81% H 5.62% Cl 9.19% N 11.09%

Example 7

Ethyl (3-benzyl-2,4-dioxo-2,3,4,5,7,8-hexahydro-1H-pyrido[4,3-d]pyrimidin-6-yl)(2-chlorophenyl)acetate hydrochloride a) 3-Benzyl-5,6,7,8-tetrahydro-1H-pyrido[4,3-d]pyrimidine- 2,4-dione A solution of 70 g of 3,6-dibenzyl-5,6,7,8-tetrahydro-1H-pyrido[4,3-d]pyrimidine-2,4-dione in 1.5 l of glacial acetic acid was debenzylated in the 6-position by hydrogenolysis on 10 g of 10% palladium/activated charcoal at 70° C. and a hydrogen pressure of 3.5 bar. After the catalyst had been filtered off, the filtrate was concentrated under reduced pressure, the residual oil was taken up with 500 ml of water and the pH was adjusted to 8 with conc. sodium carbonate solution, with stirring, to give 46 g of a white precipitate of 3-benzyl- 5,6,7,8-tetrahydro-1H-pyrido[4,3-d] pyrimidine-2,4-dione.

Melting point: 224°–226° C. (from isopropanol) $C_{14}H_{15}N_3O_2$ (MW=257.30) Calc. C 65.35% H 5.88% N 16.33% Found C 65.46% H 5.89% N 16.26% b) 3-Benzyl-5,6,7,8-tetrahydro-1H-pyrido[4,3-d]pyrimidine- 2,4-dione hydrochloride 9.4 g of 3-benzyl-5,6,7,8-tetrahydro-1H-pyrido[4,3-d]-pyrimidine-2,4-dione were suspended in 250 ml of water, the equivalent amount of 1 N HCl was added and the solution formed was filtered and concentrated under vacuum. 9.9 g of 3-benzyl-5,6,7,8-tetrahydro-1H-pyrido[4, 3-d]pyrimidine-2,4-dione hydrochloride were obtained from the residue after purification by recrystallization from isopropanol.

Melting point>300° C. $C_{14}H_{16}ClN_3O_2$ (MW=293.76) Calc. C 57.24% H 5.49% Cl 12.07% N 14.30% Found C 57.09% H 5.56% Cl 12.07% N 14.27% c) Ethyl (3-benzyl-2,4-dioxo-2,3,4,5,7,8-hexahydro-1H-pyrido[4,3-d]pyrimidin-6-yl)(2-chlorophenyl)acetate hydrochloride A mixture of 77.2 g of 3-benzyl-5,6,7,8-tetrahydro-1H-pyrido[4,3-d]pyrimidine-2,4-dione, 63 g of ethyldiisopropylamine and 126 g of ethyl chloro(2-chlorophenyl)-acetate (89% pure according to GC) in 1700 ml of dimethylformamide was stirred for 48 h at room temperature. It was concentrated under reduced pressure and the residue was worked up by extraction with dichloromethane and water. The dichloromethane phases were combined, dried and concentrated. The residue was diluted with 50 ml of dichloromethane, 1.3 equivalents of a solution of hydrochloric acid in ether were added dropwise at room temperature, with stirring, and 700 ml of tert-butyl methyl ether were added slowly. This initially gave an oil, which solidified gradually to a white mass. This ethyl (3-benzyl-2,4-dioxo- 2,3,4,5,7, 8-hexahydro-1H-pyrido[4,3-d]pyrimidin-6-yl)( 2-chlorophenyl)acetate hydrochloride was purified by recrystallization from dichloromethane/diethyl ether.

Yield: 112 g Melting point: 165°–167° C. $C_{24}H_{15}Cl_2N_3O_4$ (MW=490.39) Calc. C 58.78% H 5.14% N 8.57% Found C 58.60% H 5.19% N 8.47%

Example 8

6-(2-Hydroxyethyl)-3-methyl-5,6,7,8-tetrahydro- 1H-pyrido[4,3-d]pyrimidine-2,4-dione a) 3-Methyl-6-[2-(tetrahydropyran-2-yloxy)ethyl]- 5,6,7, 8-tetrahydro-1H-pyrido[4,3-d]pyrimidine-2,4-dione 40 g of ethyldiisopropylamine and 52.5 g of 2-( 2-chloroethoxy)tetrahydropyran (96% pure according to GC) were added to 54.5 g of 3-methyl-5,6,7,8-tetrahydro-1H-pyrido

[4,3-d]pyrimidine-2,4-dione in 1.5 l of dimethylformamide, with stirring, and the mixture was heated for 30 h at 70° C. It was concentrated under vacuum, the residue was worked up by extraction with dichloromethane and water and the combined dichloromethane phases were dried and concentrated to give 25 g of 3-methyl-6-[2-(tetrahydropyran-2-yloxy) ethyl]-5,6,7,8-tetrahydro-1H-pyrido[4,3-d]pyrimidine-2,4-dione, which was purified by bulb-tube distillation at a bath temperature of 80° C. and 0.1 mbar and by column chromatography on aluminum oxide (activity grade III) and elution with dichloromethane/ethanol (volume ratio 95:5).

6-(2-Hydroxyethyl)-3-methyl-5,6,7,8-tetrahydro- 1H-pyrido[4,3-d]pyrimidine-2,4-dione 22 g of 3-methyl-6-[2-(tetrahydropyran-2-yloxy)ethyl]-5,6,7,8-tetrahydro-1H-pyrido[4,3-d]pyrimidine-2,4-dione were dissolved in 100 ml of methanol and the pH was adjusted to 1 with conc. hydrochloric acid at room temperature, with stirring. After a further 7 h, the mixture was concentrated to dryness under reduced pressure, the residue was taken up with water and the solution was adjusted to pH 8. It was concentrated under reduced pressure and the residue was extracted exhaustively with cold ethanol. The ethanolic extract was evaporated under reduced pressure and the residue of 6-(2-hydroxyethyl)-3-methyl-5,6,7,8-tetrahydro-1H-pyrido[4,3-d]pyrimidine-2,4-dione was purified by recrystallization from isopropanol and ethanol.

Yield: 5 g Melting point: 156° C. $C_{10}H_{15}N_3O_3$ with 0.5 $H_2O$ (MW=234.25) Calc. C 51.27% H 6.88% N 17.94% Found C 51.08% H 6.62% N 17.92%

Example 9

6-(2-Hydroxy-1-phenylethyl)-3-methyl-5,6,7,8-tetrahydro- 1H-pyrido[4,3-d]pyrimidine-2,4-dione hydrochloride 17.2 g of 3-methyl-5,6,7,8-tetrahydro-1H-pyrido[4,3-d]-pyrimidine-2,4-dione, 23 g of 2-(2-chloro- 2-phenyl-ethoxy)tetrahydropyran (from 2-chloro-2-phenylethanol and 3,4-dihydro-2H-pyran) and 17.5 g of ethyldiisopropylamine were stirred for 45 h at 80° C. and 24 h at 100° C. After the reaction mixture had been concentrated under reduced pressure, the residue was worked up by extraction with dichloromethane and water. After drying, the combined dichloromethane phases were concentrated and the residue was purified by chromatography in a medium-pressure column on aluminum oxide (activity grade III) with dichloromethane/ethanol (volume ratio 97:3) as the eluent to give 8.5 g of 3-methyl-6-[2-(tetrahydropyran- 2-yloxy)-1-phenylethyl]-3-methyl-5,6,7,8-tetrahydro-1H-pyrido[4,3-d]pyrimidine-2,4-dione, from which 6-(2-hydroxy- 1-phenylethyl)-3-methyl-5,6,7,8-tetrahydro-1H-pyrido[4,3-d] pyrimidine-2,4-dione was obtained, in a mixture of 15 ml of 2 N hydrochloric acid and 25 ml of glycol dimethyl ether, by heating for 2 hours at 88° C., followed by adjustment of the pH to 7.4, concentration under reduced pressure and working-up of the resulting residue by extraction with dichloromethane and water after concentration of the dried dichloromethane phases. The product was purified by column chromatography on silica gel with dichloromethane/ethanol (volume ratio 95:5) as the eluent. 6-(2-Hydroxy-1-phenylethyl)- 3-methyl-5,6,7,8-tetrahydro-1H-pyrido[4,3-d]pyrimidine- 2,4-dione hydrochloride was obtained from the resulting 7.6 g in dichloromethane with a solution of hydrochloric acid in ether and was purified by recrystallization from isopropanol.

Yield: 4.5 g Decomposition point: 150° C. $C_{16}H_{20}ClN_3O_3$ with 0.3 $H_2O$ (MW=343.21) Calc. C 55.99% H 6.05% N 12.24% Found C 55.97% H 5.84% N 12.15%

Example 10

3-Methyl-6-(2-methylsulfinylethyl)-5,6,7,8-tetrahydro-1H-pyrido[4,3-d]pyrimidine-2,4-dione a) 3-Methyl-6-(2-methylsulfanylethyl)- 5,6,7,8-tetrahydro-1H-pyrido [4,3 -d]pyrimidine-2,4-dione 36.3 g of 3-methyl-5,6,7,8-tetrahydro-1H-pyrido[4,3-d]-pyrimidine-2,4-dione, 23 g of 1-chloro-2-methylsulfanylethane (97% pure), 17.4 g of lithium bromide and 27 g of ethyldiisopropylamine in 700 ml of dimethylformamide were stirred for 14 h at 50° C. After the reaction mixture had been concentrated under reduced pressure, the residue was taken up with 400 ml of water and 400 ml, of dichloromethane, the pH was adjusted to 8 with sodium bicarbonate, with stirring, and the mixture was worked up by extraction with dichloromethane and water. 23 g of 3-methyl-6-(2-methylsulfanylethyl)- 5,6,7,8-tetrahydro-1H-pyrido[4,3-d]pyrimidine-2,4-dione were obtained from the combined dichloromethane phases after drying, concentration and recrystallization of the residue from isopropanol.

b) 3-Methyl-6-(2-methylsulfinylethyl)-5,6,7,8-tetrahydro- 1H-pyrido[4,3-d]pyrimidine-2,4-dione 21.8 g of magnesium monoperoxyphthalate (85% pure) were added at 55° C. over a period of 15 min to a solution of 19.5 g of 3-methyl-6-(2-methylsulfanylethyl)- 5,6,7,8-tetrahydro-1H-pyrido[4,3-d]pyrimidine-2,4-dione in 200 ml of ethanol and the mixture was stirred for 2 h at 55° C. After the pH had been adjusted to 7.5, the mixture was concentrated under reduced pressure. The residue was boiled up several times with methanol, the combined methanol phases were concentrated and the residue was purified by chromatography in a medium-pressure column with silica gel using dichloromethane/methanol (volume ratio 95:5) as the eluent and by recrystallization from isopropanol.

Yield: 9.8 g Decomposition point: 228° C $C_{11}H_{17}N_3O_3S$ (MW=271.34) Calc. C 48.69% H 6.31% N 15.49% S 11.82% Found C 48.6% H 6.3% N 15.4% S 11.8%

Example 11

6-Benzyl-1-methyl-5,6,7,8-tetrahydro-3H-pyrido[4,3-d]-pyrimidine-2,4-dione hydrochloride 15.7 g of 6-benzyl-5,6,7,8-tetrahydro-1H,3H-pyrido[4,3-d]pyrimidine-2,4-dione were stirred with 8.7 g of potassium carbonate in 700 ml of dimethylformamide for 1.5 h at 50° C. 8.9 g of methyl iodide were added dropwise over 10 min and stirring was continued for 5 h at 50° C. After the suspension had been concentrated under reduced pressure, the residue was worked up by extraction with water and dichloromethane. The dried dichloromethane phases were concentrated and, in order to separate the other methylation products, namely 6-benzyl- 1,3-dimethyl-5,6,7,8-tetrahydropyrido[4,3-d]pyrimidine- 2,4-dione and 6-benzyl-3-methyl-5,6,7,8-tetrahydro-1H-pyrido[4,3-d]pyrimidine-2,4-dione, from the desired 6-benzyl-1-methyl-5,6,7,8-tetrahydro-3H-pyrido[4,3-d]pyrimidine-2,4-dione, the residue was subjected to chromatography on silica gel in a medium-pressure column with dichloromethane/ethanol (volume ratio 98:2) as the eluting mixture. The fractions containing pure 6-benzyl- 1-methyl-5,6,7,8-tetrahydro-3H-pyrido[4,3-d]pyrimidine- 2,4-dione were precipitated as 6-benzyl-1-methyl- 5,6,7,8-tetrahydro-3H-pyrido[4,3-d]pyrimidine-2,4-dione hydrochloride in dichloromethane with a solution of HCl in ether. The product was recrystallized from water.

Yield: 2.6 g Decomposition point: 293° C. $C_{15}H_{18}ClN_3O_2$ (MW=307.78) Calc. C 58.54% H 5.90% Cl 11.52% N 13.65% Found C 58.34% H 5.92% Cl 11.44% N 13.58%

Example 12

6-(4-Hydroxybutyl)-3-methyl-5,6,7,8-tetrahydro-1H-pyrido[4,3-d]pyrimidine-2,4-dione a) 3-Methyl-6-[4-(tetrahydropyran-2-yloxy)butyl]-5,6,7,8-tetrahydro-1H-pyrido[4,3-d]pyrimidine-2,4-dione 27 g of ethyldiisopropylamine, 18 g of lithium bromide and 46 g of 2-(4-chlorobutoxy) tetrahydropyran (86.3% pure according to GC) were added to 36.3 g of 3-methyl-5,6,7,8-tetrahydro-1H-pyrido[4,3-d]pyrimidine-2,4-dione in 1 l of dimethylformamide, with stirring, and the mixture was stirred for 5 h at 70° C. It was concentrated under reduced pressure and 34.5 g of crude 3-methyl-6-[4-(tetrahydropyran-2-yloxy)butyl]-5,6,7,8-tetrahydro-1H-pyrido[4,3-d]pyrimidine-2,4-dione were obtained after working-up of the residue by extraction with dichloromethane and water and after drying and concentration of the combined dichloromethane phases, and this crude product was purified by column chromatography on aluminum oxide (actiVity grade III) and elution with dichloromethane/ethanol (volume ratio 90:10).

b) 6-(4-Hydroxybutyl)-3-methyl-5,6,7,8-tetrahydro-1H-pyrido[4,3-d]pyrimidine-2,4-dione 12 g of 3-methyl-6-[4-(tetrahydropyran-2-yloxy)butyl]-5,6,7,8-tetrahydro-1H-pyrido[4,3-d]pyrimidine-2,4-dione were dissolved in 150 ml of methanol and 150 ml of water and the pH was adjusted to i with conc. hydrochloric acid at 20°–25° C., with stirring. After 7 h at room temperature, the mixture was concentrated to dryness under reduced pressure, the residue was taken up with water and the solution was adjusted to pH 7.8. It was concentrated under vacuum and the residue was extracted exhaustively with hot ethanol. The ethanolic extract was evaporated under reduced pressure and the crude 6-(4-hydroxybutyl)-3-methyl-5,6,7,8-tetrahydro-1H-pyrido-[4,3-d]pyrimidine-2,4-dione was purified by column chromatography on silica gel with dichloromethane/methanol (volume ratio 90:10) and by recrystallization from isopropanol.

Yield: 3.2 g Melting point: 121° C. $C_{12}H_{19}N_3O_3$ (MW=253.3) Calc. C 56.90% H 7.57% N 16.59% Found C 56.65% H 7.67%

Example 13

6-(3-Methyl-2,4-dioxo-2,3,4,5,7,8-hexahydro-1H-pyrido[4,3-d]pyrimidin-6-yl)hexanoic acid hydrochloride a) Tert-butyl 6-(3-methyl-2,4-dioxo-2,3,4,5,7,8-hexa-hydro-1H-pyrido [4,3-d]pyrimidin-6-yl)hexanoate 22 g of ethyldiisopropylamine and 38 g of tert-butyl 6-bromohexanoate (from 6-bromohexanoic acid and isobutylene in dichloromethane in the presence of conc. sulfuric acid as catalyst) were added to 27.2 g of 3-methyl-5,6,7,8-tetrahydro-1H-pyrido[4,3-d]pyrimidine- 2,4-dione in 0.5 l of dimethylformamide, with stirring, and the mixture was stirred for 72 h at room temperature. It was concentrated under reduced pressure, the residue was worked up by extraction with dichloromethane and water (adjusted to pH 8) and the combined and dried dichloromethane phases were concentrated to give 55 g of an oily crude product, which was purified by recrystallization from diethyl ether/petroleum ether to give 31 g of tert-butyl 6-(3-methyl-2,4-dioxo-2,3,4,5,7,8-hexahydro-1H-pyrido[4,3-d]pyrimidin-6-yl)-hexanoate.

b) 6-(3-Methyl-2,4-dioxo-2,3,4,5,7,8-hexahydro-1H-pyrido[4,3-d]pyrimidin-6-yl)hexanoic acid hydrochloride A solution of 8.3 g of reft-bury16-(3-methyl-2,4-dioxo-2,3,4,5,7,8-hexahydro-1H-pyrido[4,3-d]pyrimidin-6-yl)hexanoate in 300 ml of dichloromethane was saturated with HCl gas at 0° C. and subsequently stirred for 1 h at 0° C. After the reaction mixture had been concentrated under reduced pressure, the residue was taken up with water and the pH was adjusted to 8.5 with sodium hydroxide solution. After extraction with dichloromethane, the aqueous phase was purified by chromatography on an Amberlyst A 26 ion exchanger (elution with 0.25 N HCl). After concentration of the aqueous eluate, this gave 5.9 g of 6-(3-methyl- 2,4-dioxo-2,3,4,5,7,8-hexahydro-1H-pyrido[4,3-d]pyrimidin-6-yl)hexanoic acid hydrochloride, which was purified by recrystallization from ethanol/water.

Yield: 5 g Decomposition point: 110° C. $C_{14}H_{22}ClN_3O_4$ with 1 $H_2O$ (MW=349.82) Calc. C 48.07% H 6.92% Cl 10.13% N 12.01% Found C 48.17% H 6.73% Cl 10.15% N 11.96%

Example 14

1-(2-Hydroxyethyl)-3,6-dimethyl-5,6,7,8-tetrahydro-1H-pyrido[4,3-d]pyrimidine-2,4-dione a) 3,6-Dimethyl-5,6,7,8-tetrahydro-1H-pyrido[4,3-d]-pyrimidine-2,4-dione hydrochloride 63.4 ml of methyl iodide were added dropwise over a period of 15 win at an initial temperature of 21° C. to 181 g of 3-methyl-5,6,7,8-tetrahydro-1H-pyrido[4,3-d]-pyrimidine-2,4-dione and 178 ml of ethyldiisopropylamine in 3 l of DMF, with stirring (the temperature rising to 35° C.). After stirring for a further 5 h at room temperature, the reaction mixture was concentrated under reduced pressure and the residue was worked up by extraction with dichloromethane and water. The combined aqueous phases were concentrated at 70° C. under reduced pressure until a precipitate formed, and the precipitate (39.5 g), made up predominantly of 3,6,6-trimethyl- 5,6,7,8-tetrahydro-1H-pyrido[4,3-d]pyrimidine-2,4-dione hydroiodide, was filtered off. The mother liquor was concentrated and the residue was boiled up with 1 l of ethanol to give a further 15.7 g of an insoluble residue made up predominantly of 3,6,6-trimethyl- 5,6,7,8-tetrahydro-1H-pyrido[4,3-d]pyrimidine-2,4-dione hydroiodide. After purification by extraction by boiling with methanol, the combined precipitates gave 45 g of pure 3,6,6-trimethyl-5,6,7,8-tetrahydro-1H-pyrido[4,3-d]pyrimidine-2,4-dione hydroiodide.

Decomposition point: 288° C. $C_{10}H_{16}IN_3O_2$ (MW=337.16) Calc. C 35.62% H 4.78% I 37.64 % N 12.46% Found C 35.56% H 4.74% I 37.86% N 12.38%

The methanolic and ethanolic mother liquors were combined and concentrated under reduced pressure. The residue, made up predominantly of 3,6-dimethyl-5,6,7,8-tetrahydro-1H-pyrido[4,3-d]pyrimidine-2,4-dione hydroiodide, was purified by chromatography on an Amberlyst A 15 strongly acidic ion exchanger using 1 N HCl as the eluent. After concentration of the appropriate fractions and drying of the residue, 55 g of 3,6-dimethyl- 5,6,7,8-tetrahydro-1H-pyrido[4,3-d]pyrimidine-2,4-dione hydrochloride were obtained as a white powder.

b) 3,6-Dimethyl-1-[2-(tetrahydropyran-2-yloxy) ethyl]-5,6,7,8-tetrahydro-1H-pyrido[4,3-d]pyrimidine-2,4-dione 11.6 g of 3,6-dimethyl-5,6,7,8-tetrahydro-1H-pyrido[4,3-d]pyrimidine-2,4-dione hydrochloride were added over a period of 5 min to a suspension of 3 g of sodium hydride in 75 ml of DMF, the temperature rising to 60° C. After stirring for 1.5 h at 60° C., 11.6 g of 2-(2-bromoethoxy)-tetrahydropyran were added dropwise over a period of 10 min. After stirring for a further 8 h at 60° C., the reaction mixture was concentrated under reduced pressure and the residue was worked up by extraction with dichloromethane and water. The dichloromethane phases were combined, dried and concentrated. After bulb-tube distillation at 50° C. and 0.05 mbar and column chromatography on aluminum oxide (activity grade III) with dichloromethane/ethanol (volume ratio 98:2), 3 g of 3,6-dimethyl-1-[2-(tetrahydropyran-2-yloxy)ethyl]- 5,6,7,8-tetrahydro-1H-pyrido[4,3-d]pyrimidine-2,4-dione were obtained from the residue.

1-(2-Hydroxyethyl)-3,6-dimethyl-5,6,7,8-tetrahydro-1H-pyrido[4,3-d]pyrimidine-2,4-dione 3 g of 3,6-dimethyl-1-[2-(tetrahydropyran-2-yloxy)ethyl]- 5,6,7,8-tetrahydro-1H-pyrido[4,3-d]pyrimidine-2,4-dione were dissolved in 150 ml of water and the pH was adjusted to 1 with conc. hydrochloric acid at 20°–25° C., with stirring. After stirring for 5 h at room temperature, 2 N sodium hydroxide solution was added dropwise to pH 8 and the reaction mixture was concentrated under reduced pressure. After azeotropic drying with ethanol, the residue was purified by chromatography on silica gel in a medium-pressure column with dichloromethane/methanol (volume ratio 85:15) and by recrystallization from dichloromethane/diethyl ether.

Yield: 0.7 g Melting point: 120°–122° C. $C_{11}H_{17}N_3O_3$ (MW=239.28) Calc. C 55.22% H 7.16% N 17.56% Found C 55.02% H 7.32% N 17.64%

Example 15

3-Benzyl-6.-methyl-5,6,7,8-tetrahydro-1H-pyrido[4,3-d]pyrimidine-2,4-dione hydrochloride 6.5 g of 3-benzyl-5,6,7,8-tetrahydro-1H-pyrido[4,3-d]pyrimidine-2,4-dione hydrochloride were added at 0° C. to a mixture of 5.5 ml of 90% formic acid and 4 ml of 37% formaldehyde, with stirring. After heating for 8 h at the reflux temperature, 26.5 ml of i N hydrochloric acid were added at room temperature and the mixture was then concentrated under reduced pressure. After recrystallization from isopropanol/water, 3-benzyl- 6-methyl-5,6,7,8-tetrahydro-1H-pyrido[4,3-d]pyrimidine- 2,4-dione hydrochloride was obtained from the residue.

Yield: 5.7 g Decomposition point: 278° C. $C_{15}H_{18}ClN_3O_2$ with 0.2 $H_2O$ (MW=311.39) Calc. C 57.86% H 5.96% Cl 11.39% N 13.49% Found C 57.81% H 5.72% Cl 11.71% N 13.45%

Pharmacological tests

A) Antithrombotic activity

Thrombotic incidents are an important factor in the origin and course of cerebral or peripheral arterial occlusive diseases and other indications claimed for this group of substances. Thus the compounds according to the invention were tested for the inhibition of laser-induced thrombosis. These tests were performed on female Sprague-Dawley rats with a bodyweight of ca. 200 g. The 10 animals were premedicated sc with 0.1 mg of atropine sulfate and anesthetized ip with 100 mg of ketamine hydrochloride and 4 mg of xylazine per kg of body weight. The test was carried out using arterioles and venoles of the mesenterium coated with degassed paraffin oil and having a diameter of ca. 13 μm. The beam of the 3 W argon laser (Spectra-Physics, Darmstadt) was introduced coaxially into the inverted ray path of a microscope (ICM 405, LD ®Epiplan 40 or 60, Zeiss, Oberkochen) by means of a ray adapting and adjusting unit. The wavelength used was 514.5 run with a power of 30 mW above the objective. The exposure time per individual charge was 1/15 sec. All the measurement procedures were photographed by video camera (®Trinicon tube, Sony, Cologne) and stored on a recorder (®Sony U-matics ¾"). The test substances were administered to the experimental animals in various doses I hour before the start of the experiment in the case of oral administration and 10 min in the case of iv administration; control animals received the same amount of the placebo. The substances were administered as a single dose once a day or once a day over several days. The evaluation was made by counting the number of laser charges required to produce a parietal thrombosis with a minimum size of half the vessel diameter. This means that the larger the number of laser charges, the more effective are the preparations in this test. The percentage inhibition of thrombosis is given in Table 1.

TABLE 1

| Compound | Structure | Percentage inhibition of thrombosis, m.p. (or d) and preparation | | | | | | | |
|---|---|---|---|---|---|---|---|---|---|
| | | 10 po | 1 iv | 3 iv | 10 iv | 1 ip | 30 ip | M.p. | Preparation |
| 1 | 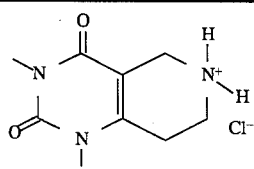 | +33 | | | | | | 304 d | see ex. 1 |
| 2 | 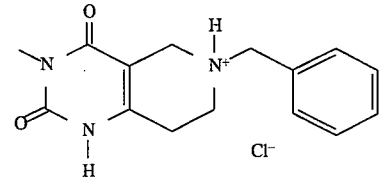 | +41 | +20 | | | | | 298 d | see ex. 2 |

TABLE 1-continued

| Compound | Structure | Percentage inhibition of thrombosis, m.p. (or d) and preparation | | | | | | M.p. | Preparation |
|---|---|---|---|---|---|---|---|---|---|
| | | 10 po | 1 iv | 3 iv | 10 iv | 1 ip | 30 ip | | |
| 3 | 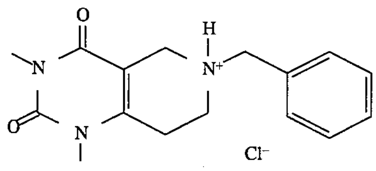 | +33 | +26 | | | | | 141–143 | see ex. 3 |
| 4 | 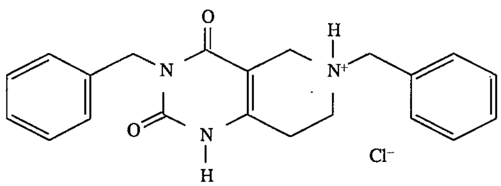 | +49 | | | | | | 300 d | see ex. 4 |
| 5 | 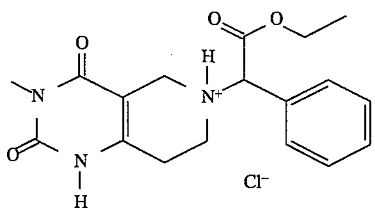 | +39 | +39 | | | −7 | | 166 d | see ex. 5 |
| 6 | 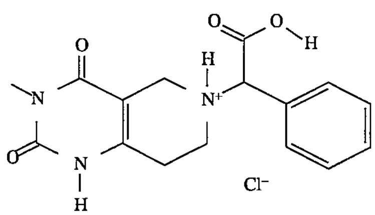 | −4 | | +18 | | +35 | | 237 d | see ex. 6 |
| 7 | 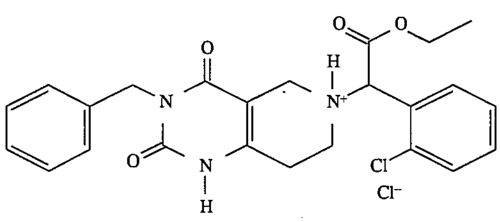 | +23 | | | | | | 165–167 | see ex. 7 |
| 8 | 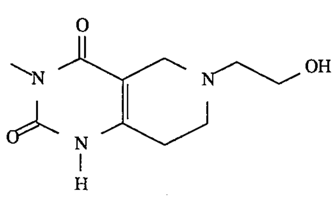 | +36 | | +40 | | | | 156 | see ex. 8 |
| 9 | 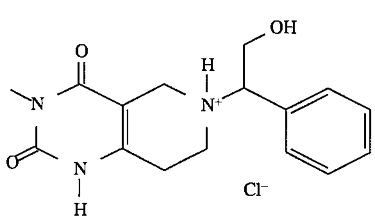 | +23 | | | | | | 150 d | see ex. 9 |

TABLE 1-continued

| Compound | Structure | 10 po | 1 iv | 3 iv | 10 iv | 1 ip | 30 ip | M.p. | Preparation |
|---|---|---|---|---|---|---|---|---|---|
| 10 | 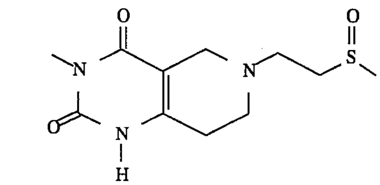 | +15 | 0 | +29 | +11 | | | 228 d | see ex. 10 |
| 11 | 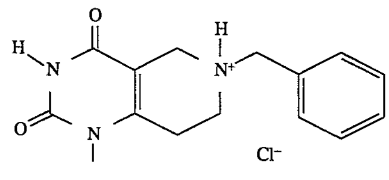 | | | | +16 | | | 293 d | see ex. 11 |
| 12 | 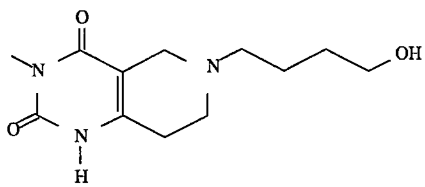 | +23 | | +15 | +32 | | | 121 | see ex. 12 |
| 13 | 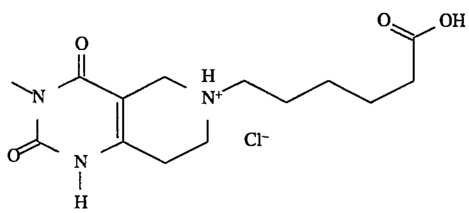 | +18 | | | | | | 110 d | see ex. 13 |
| 14 | 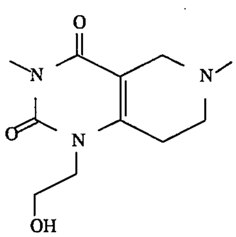 | +29 | | | +20 | | | 120–122 | see ex. 14 |
| 15 | 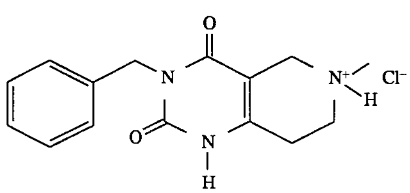 | +32 | | | +16 | | | 278 d | see ex. 15 |
| 16 | 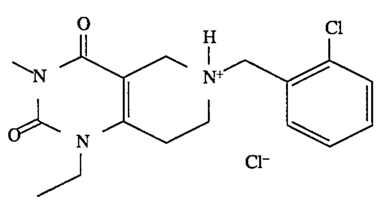 | +43 | +21 | +36 | +56 | | | 192–193 | a ex. 3 |

TABLE 1-continued

| Compound | Structure | 10 po | 1 iv | 3 iv | 10 iv | 1 ip | 30 ip | M.p. | Preparation |
|---|---|---|---|---|---|---|---|---|---|
| 17 | | +43 | | | | | | 237 d | a ex. 5 |
| 18 | | +23 | | | | | | 300 d | a ex. 5 |
| 19 | | +46 | +22 | +31 | | | +35 | 148 d | a ex. 5 |
| 20 | | +13 | | +4 | | | +51 | 216 d | a ex. 6 |
| 21 | | +27 | | | | | | 153 d | a ex. 7 |
| 22 | | +31 | | | | | | 161 d | a ex. 5 |
| 23 | | +36 | | | | | | 291 d | a ex. 1c |

TABLE 1-continued

| Compound | Structure | 10 po | 1 iv | 3 iv | 10 iv | 1 ip | 30 ip | M.p. | Preparation |
|---|---|---|---|---|---|---|---|---|---|
| 24 | 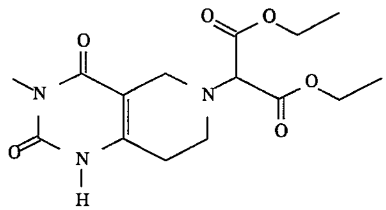 | +16 | | | | | | 172–173 | a ex. 5 |
| 25 | 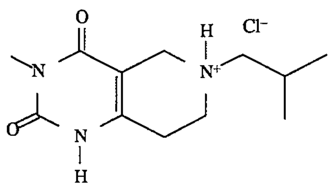 | +16 | | | | | | 245 d | a ex. 5 |
| 26 | 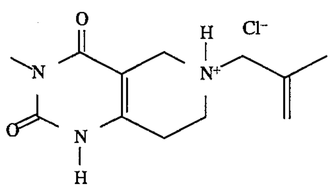 | +34 | +18 | +38 | +31 | | | 238 d | a ex. 5 |
| 27 | 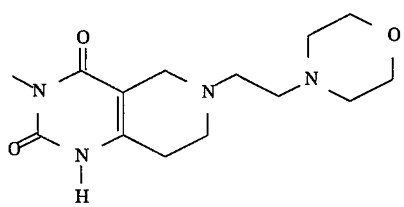 | +16 | | | | | | 186 d | a ex. 5 |
| 28 | 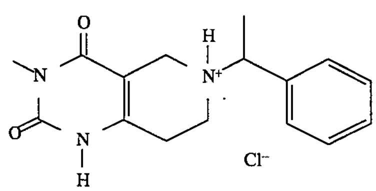 | +27 | | +25 | | | | 274 d | a ex. 5 |
| 29 | 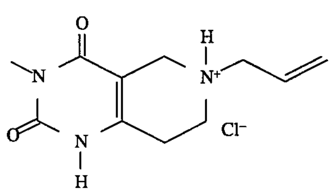 | +27 | | +29 | | | | 215 d | a ex. 5 |
| 30 | 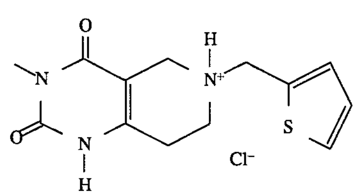 | +12 | | | | | | 272 d | a ex. 5 |

TABLE 1-continued
| Compound | Structure | 10 po | 1 iv | 3 iv | 10 iv | 1 ip | 30 ip | M.p. | Preparation |
|---|---|---|---|---|---|---|---|---|---|
| 31 | 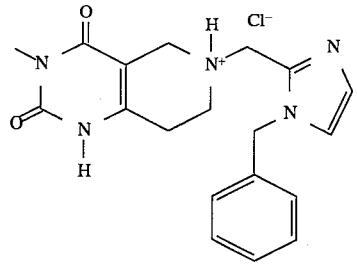 | +20 | | | | | | 265 d | a ex. 5 |
| 32 | 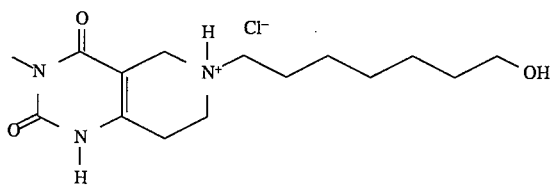 | +11 | | +15 | +32 | | | 188–190 | a ex. 5 |
| 33 | 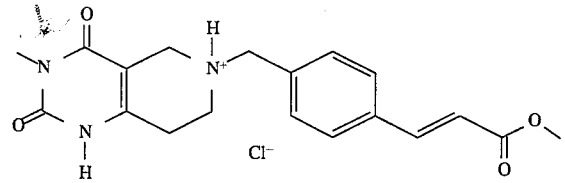 | +17 | +10 | +3 | | | | 237 | a ex. 5 |
| 34 | 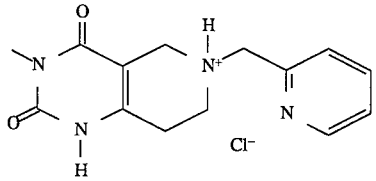 | +17 | | +2 | | | | 268–269 | a ex. 5 |
| 35 | 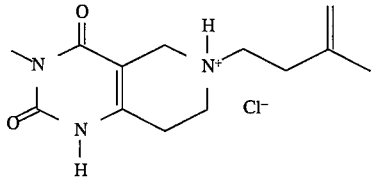 | | | | +32 | | | 220 d | a ex. 5 |
| 36 | 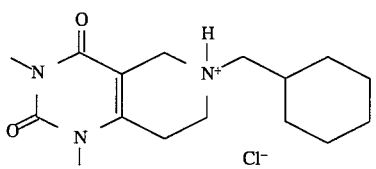 | +16 | | | | | | 243 d | a ex. 5 |
| 37 | 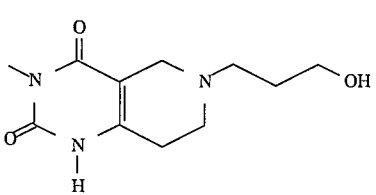 | +33 | +3 | +13 | +31 | | | 173–174 | a ex. 8 |

TABLE 1-continued

| Compound | Structure | 10 po | 1 iv | 3 iv | 10 iv | 1 ip | 30 ip | M.p. | Preparation |
|---|---|---|---|---|---|---|---|---|---|
| 38 | 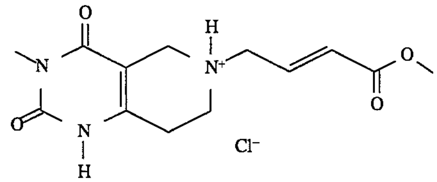 | +23 | | +4 | | | | 225 d | a ex. 5 |
| 39 | 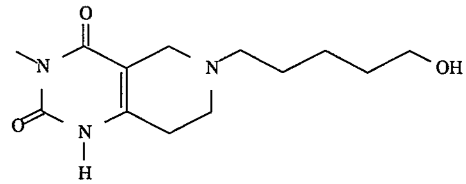 | +30 | +31 | +40 | | | | 132–134 | a ex. 8 |
| 40 | 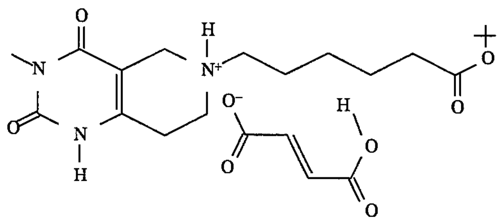 | +12 | | | | | | 190 d | a ex. 13a |
| 41 | 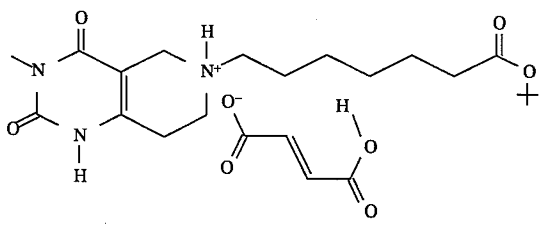 | +22 | | | | | | 180 d | a ex. 13a |
| 42 | 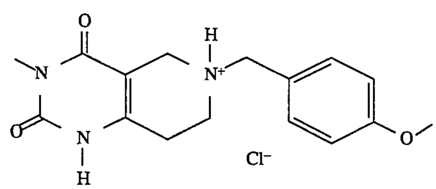 | | | | +14 | | | 232 | a ex. 5 |
| 43 | 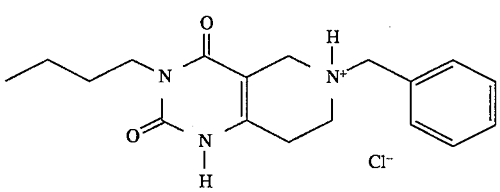 | +6 | +8 | | | | | 255 d | a ex. 1 |
| 44 | 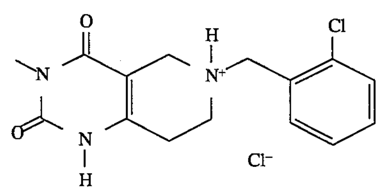 | +27 | | | | | | 243 d | a ex. 5 |

TABLE 1-continued

| | | Percentage inhibition of thrombosis, m.p. (or d) and preparation | | | | | | | |
|---|---|---|---|---|---|---|---|---|---|
| Compound | Structure | 10 po | 1 iv | 3 iv | 10 iv | 1 ip | 30 ip | M.p. | Preparation |
| 45 | [structure] | +11 | | +20 | | | | 258 | a ex. 2 |

B) Action on the contractility of the skeletal muscle after chronic ischemia

Ideas about the pathophysiology of chronic peripheral arterial occlusive disease have changed in recent years as interest has shifted increasingly from the macrocirculation to the microcirculation= disorders in the microcirculation manifest themselves in an inadequate supply of substrates with consequent tissue ischemia, which in turn leads to impairment of the function of the extremity in question. The compounds according to the invention were tested for their function-improving action by means of measurements of the contractile force in the ischemic skeletal muscle using the experimental set-up described below.

The experimental animals used were male Wistar rats with a body weight of 380 to 410 g. With the animals under hexobarbital narcosis (®Evipan Sodium, 200 mg/kg body weight ip), a monolateral ligature of the right femoral artery was made in the groin. After dusting with penicillin sulfonamide powder for the antibiotic protection of the wound, the small surgical wound was closed and the animals were observed continuously until fully awake. One week later, oral administration of the substance with a stomach tube was started (6 mg/kg body weight, carboxymethyl cellulose sodium suspension) and was continued for 7 days (single administration per day, ca. 7.30 am to 8.30 am). The contractile force was measured 24 h after the last administration of the substance so as to exclude acute effects, the experimental protocol being as follows:

The animals were narcotized with ®Nembutal (pentobarbital sodium, 35 mg/kg body weight ip), the muscles of the extremity in question were exposed (gastrocnemius-plantaris-soleus group) and the tendon was connected to a force transducer with a preload of 50 g. A superfusion with isotonic solution (37° C.) served to avoid dehydration and cooling. The mean arterial blood pressure was recorded continuously via a cannulated carotid artery with the aid of a hemodynamometer in order to monitor the physiological state of the animals during the experiment. All the animals breathed spontaneously through an inserted endotracheal tube.

After these preparations had been made, the muscle was caused to contract by direct electrical stimulation (2.5 mA, 2 Hz) (Stimulator I, Hugo Sachs, Federal Republic of Germany). The measurement parameter used for the action of the preparation was the absolute contractile force in grams after 5 minutes of stimulation. The change in the contractile force in comparison with the ischemic control muscle is given as the percentage change at this time (see Table 2).

TABLE 2

| | | Change in the contractile force (%) in comparison with the ischemic control muscle |
|---|---|---|
| Compound | Structure | PVD fatigue model: 6 mg/kg po |
| 2 | [structure] | +136 |
| 16 | [structure] | +148 |

TABLE 2-continued

| | Change in the contractile force (%) in comparison with the ischemic control muscle | |
|---|---|---|
| Compound | Structure | PVD fatigue model: 6 mg/kg po |
| 20 | 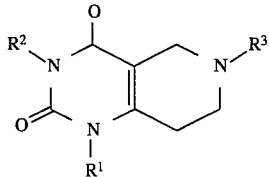 | +137 |
| 23 | | +129 |
| 8 | | +151 |
| 26 | | +114 |
| 37 | | +45 |

We claim:
1. A compound of the formula I:

$$\text{(I)}$$

and physiologically acceptable salts of the compound of the formula I, and optionally stereoisomeric forms of the compound of the formula I, in which $R^1$ is
  a) a hydrogen atom,
  b) $(C_1-C_4)$-alkyl,
  c) ω-hydroxy-$(C_2-C_4)$-alkyl,
  d) benzyl,
  e) benzyl monosubstituted or polysubstituted on the ring by
    1) a halogen atom
    2) nitride or
    3) methoxy,
  f) (ω-1)-$(C_3-C_5)$-alkenyl or
  g) (ω-1)-$(C_3-C_5)$-alkenyl substituted on the (ω-1) carbon by methyl, $R^2$ is
  a) a hydrogen atom,
  b) $(C_1-C_6)$-alkyl,
  c) benzyl or
  d) benzyl monosubstituted or polysubstituted on the ring by
    1) a fluorine, chlorine, bromine or iodine atom,
    2) nitrile or
    3) methoxy and $R^3$ is
  a) a hydrogen atom,
  b) $(C_1-C_8)$-alkyl,
  c) cyclohexylmethyl,
  d) ω-hydroxy-$(C_2-C_8)$-alkyl,
  e) (ω-1)-$(C_3-C_5)$-alkenyl, f) (ω-1)-(C$_3$-C$_5$)-alkenyl substituted on the (ω-1) carbon by methyl,
g) benzyl,
h) benzyl 1) monosubstituted or polysubstituted on the ring by
  1.1 a fluorine, chlorine, bromine or iodine atom,
  1.2 nitrile,
  1.3 methoxy or
  1.4 —CH=CH—COOR$^4$, in which R$^4$ is a hydrogen atom or (C$_1$-C$_4$)-alkyl,
and/or 2) monosubstituted in the α-position of the benzyl radical by
  2.1 methyl,
  2.2 hydroxymethyl,
  2.3 carboxyl or
  2.4

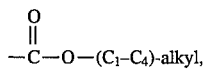
—C—O—(C$_1$-C$_4$)-alkyl, i) —(CH$_2$)$_n$—COOR$^5$, in which
  n is an integer from 1 to 8 and
  R$^5$ is a) a hydrogen atom or b) (C$_1$-C$_4$)-alkyl,
k) —CH$_2$—CH=CH—COOR$^6$, in which R$^6$ is (C$_1$-C$_4$)-alkyl,
l) pyridylmethyl,
m) 1-benzyl imidazol-2-ylmethyl,
n) —CH(COOR$^6$)$_2$, in which R$^6$ is (C$_1$-C$_4$)-alkyl,
o) ω-morpholin-4-yl-(C$_2$-C$_4$)-alkyl,
p) 2-methylsulfinylethyl or
q) thienylmethyl, with the exception of the compound of the formula I in which R$^1$ and R$^2$ are hydrogen atoms.

2. A compound of the formula I:

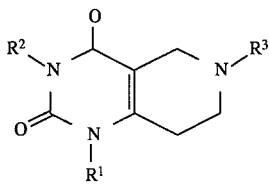

(I)

or a physiologically acceptable salt of the compound of the formula I, or optionally a stereoisomeric form of the compound of the formula I, in which
R$^1$ is
  a) a hydrogen atom,
  b) (C$_1$-C$_4$)-alkyl,
  c) 2-hydroxyethyl,
  d) benzyl, or
  e) 2-methylalkyl;
R$^2$ is
  a) a hydrogen atom,
  b) (C$_1$-C$_6$)-alkyl, or
  c) benzyl; and
R$^3$ is
  a) a hydrogen atom,
  b) (C$_1$-C$_8$)-alkyl,
  c) cyclohexylmethyl,
  d) ω-hydroxy-(C$_2$-C$_8$)-alkyl,
  e) (ω-1)-(C$_3$-C$_5$)-alkenyl,
  f) (ω-1)-(C$_3$-C$_5$)-alkenyl substituted on the (ω-1) carbon by methyl,
  g) benzyl,
  h) benzyl
    1) monosubstituted or polysubstituted on the ring by
      i) 1.1 a halogen atom,
      ii) 1.2 nitrile,
      iii) 1.3 methoxy, or
      iv) 1.4 —CH=CH—COOR$^4$, in which R$^4$ is methyl or ethyl; and/or
    2) monosubstituted in the ω-position of the benzyl radical by
      i) 2.1 methyl,
      ii) 2.2 hydroxymethyl,
      iii) 2.3 carboxyl,
      iv)

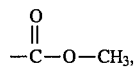
—C—O—CH$_3$, or
v)

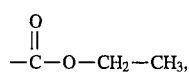
—C—O—CH$_2$—CH$_3$, i) —(CH$_2$)$_n$COOR$^5$, in which
  n is an integer from 1 to 8 and
  R$^5$ is a) a hydrogen atom or
    b) (C$_1$-C$_2$)-alkyl,
k) —CH2—CH=CH—COOR$^6$, in which R$^6$ is (C$_1$-C$_2$)-alkyl,
l) 2 -pyridylmethyl,
m) 1-benzylimidazol-2-ylmethyl,
n) —CH(COOR$^6$)$_2$, in which R$^6$ is (C$_1$-C$_2$)-alkyl,
o) ω-morpholin-4-ylethyl,
p) 2-methylsulfinylethyl or
q) 2-thienylmethyl, with the exception of the compound of the formula I in which R$^1$ and R$^2$ are hydrogen atoms.

3. A pharmaceutical composition containing of at least one compound of the formula I as claimed in claim 1, and/or at least one physiologically acceptable of the formula I, in addition to physiologically acceptable adjuncts and excipients and optionally other additives.

4. A method of treating or preventing microcirculatory disorders comprising administering an effective amount in a mammal of at least one compound of the formula I as claimed in claim 1.

5. A method of treating or preventing microcirculatory disorders comprising
  administering to a mammal, an effective amount of the pharmaceutical composition as claimed in claim 3.

6. A compound of the formula I as claimed in claim 2 in which
R$^1$ is
  a) a hydrogen atom,
  b) methyl, or
  c) ethyl;
R$^2$ is
  a) a hydrogen atom,
  b) (C$_1$-C$_4$)-alkyl, or
  c) benzyl; and
R$^3$ is
  a) a hydrogen atom,
  b) (C$_1$-C$_8$)-alkyl,
  cyclohexylmethyl,
  d) ω-hydroxy-(C$_2$-C$_4$)-alkyl,
  e) (ω-1)-(C$_3$-C$_5$)-alkenyl,
  f) (ω-1)-(C$_3$-C$_5$)-alkenyl substituted on the (ω-1) carbon by methyl, g) benzyl, h) benzyl
1) monosubstituted or polysubstituted on the ring by
   i) a fluorine or chlorine atom,
   ii) nitrile,
   iii) methoxy, or
   iv) —CH=CH—COOR$^4$, in which R$^4$ is methyl or ethyl, and/or
2) monosubstituted in the α-position of the benzyl radical by
   i) carboxyl,
   ii) 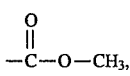
   or
   iii) 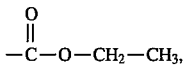

i) 2-thienylmethyl, with the exception of the compound of the formula I in which R$^1$ and R$^2$ are hydrogen atoms.

* * * * *

UNITED STATES PATENT AND TRADEMARK OFFICE
CERTIFICATE OF CORRECTION

PATENT NO. : 5,556,854
DATED : September 17, 1996
INVENTOR(S) : Harald FURRER et al.

It is certified that error appears in the above-indentified patent and that said Letters Patent is hereby corrected as shown below:

Title page, Item [57], in the Abstract, in formula I;

In the Specification, column 1, line 20, in formula I;

Claim 1, column 37, line 50, in formula I; and

Claim 2, column 39, line 35, in formula I:

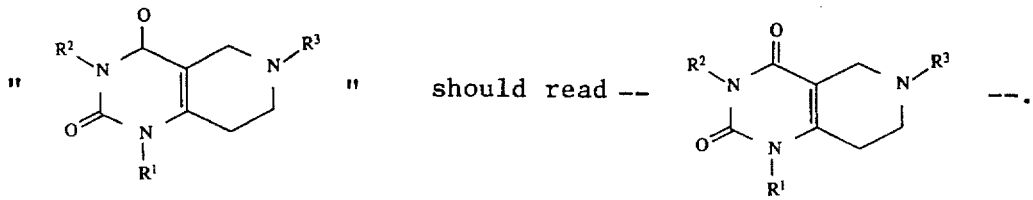

Claim 1, column 37, line 67, after "atom" insert --,--.

Claim 1, column 38, line 47, "nitride" should read --nitrile--.

UNITED STATES PATENT AND TRADEMARK OFFICE
CERTIFICATE OF CORRECTION

PATENT NO. : 5,556,854
DATED : September 17, 1996
INVENTOR(S) : Harald FURRER et al.

It is certified that error appears in the above-indentified patent and that said Letters Patent is hereby corrected as shown below:

Claim 1, column 39, line 26, "1-benzyl imidazol-2-ylmethyl," should read --1-benzylimidazol-2-ylmethyl,--.

Claim 2, column 40, line 25, "—CH2—CH" should read ---CH$_2$—CH--.

Claim 3, column 40, line 35, after "containing", delete "of".

UNITED STATES PATENT AND TRADEMARK OFFICE
CERTIFICATE OF CORRECTION

PATENT NO. : 5,556,854
DATED : September 17, 1996
INVENTOR(S) : Harald FURRER et al.

It is certified that error appears in the above-indentified patent and that said Letters Patent is hereby corrected as shown below:

Claim 3, column 40, line 37, after "acceptable", insert --salt of a compound--.

Claim 6, column 40, line 63, before "cyclohexylmethyl", insert --c) --.

Signed and Sealed this

Twenty-third Day of September, 1997

Attest:

BRUCE LEHMAN

Attesting Officer

Commissioner of Patents and Trademarks